United States Patent [19]

Martin et al.

[11] Patent Number: 4,784,833
[45] Date of Patent: Nov. 15, 1988

[54] APPARATUS FOR DETERMINING CHEMICAL STRUCTURE

[75] Inventors: Stephen J. Martin, Katy; Raymond D. Worden, Houston, both of Tex.

[73] Assignee: Ruska Laboratories, Inc., Houston, Tex.

[21] Appl. No.: 876,228

[22] Filed: Jun. 19, 1986

[51] Int. Cl.$^4$ .................. G01N 25/22; G01N 31/12
[52] U.S. Cl. .......................................... 422/80; 422/93; 422/98; 436/157; 436/158; 436/159; 436/160
[58] Field of Search .............................. 422/80, 93, 98; 436/157, 158, 159, 160

[56] References Cited
U.S. PATENT DOCUMENTS 3,475,131 10/1969 Keulemans .......................... 422/80
4,244,917 1/1981 Woods et al. ..................... 422/80 X Primary Examiner—Barry S. Richman
Assistant Examiner—Lynn M. Kummert
Attorney, Agent, or Firm—Browning, Bushman, Zamecki & Anderson

[57] ABSTRACT

A pyrolysis apparatus useful in analyzing complex chemical substances including a pyrolysis chamber formed in a tubular member of fused quartz, the apparatus having a mixing chamber formed from a fused quartz material wherein pyrolysis components from a sample to be analyzed are mixed with hydrogen prior to being subjected to detection in an analyzer such as a flame ionization detector.

4 Claims, 3 Drawing Sheets

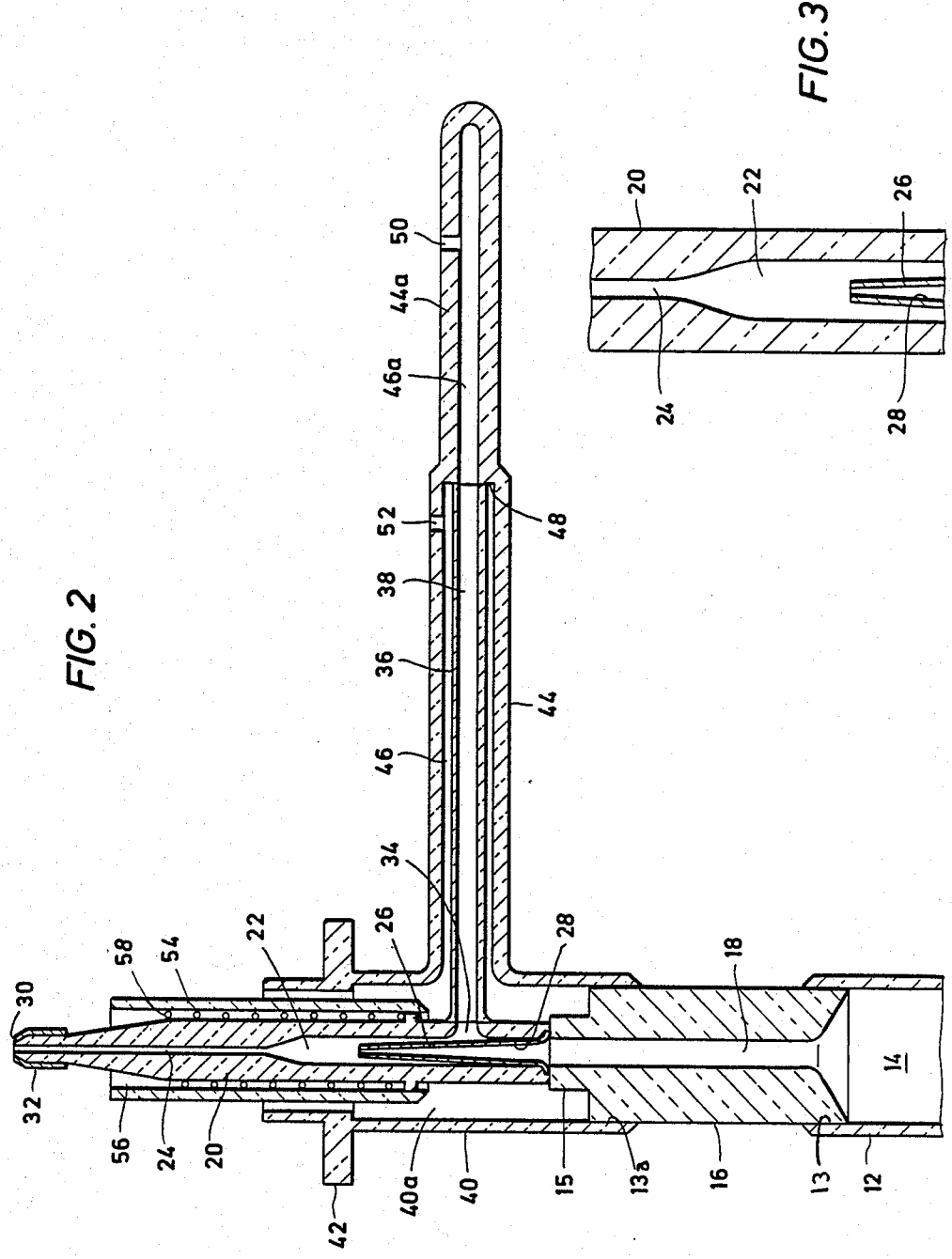
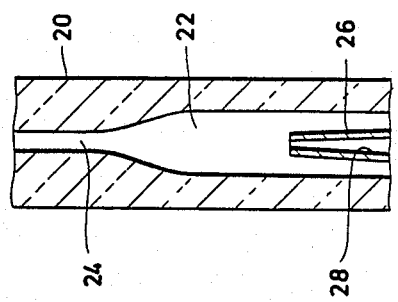

APPARATUS FOR DETERMINING CHEMICAL STRUCTURE

BACKGROUND OF THE INVENTION

1. Field of the Invention

The present invention relates to an apparatus useful in identifying the chemical nature or structure of substances, and, more particularly, an apparatus for pyrolyzing substances to generate volatile and breakdown components of such substances.

2. Description of the Prior Art

Numerous analytical techniques such as gas chromotography, mass spectroscopy, infrared spectroscopy, etc. are available for analyzing chemical compounds and mixtures. However, many, complex chemical substances cannot be analyzed effectively by such techniques because of the myriad of individual chemical compounds present in the substances or because the substance is a highly complex material, e.g. a polymer.

One area where analysis of complex chemical substances is extremely important involves the oil and gas industry. It is common, during drilling an oil or gas well, to chemically analyze formation samples from the well to determine the presence of commercial quantities of hydrocarbon material. Typically, such analyses have been carried out through laborious and time consuming chemical techniques which must be carried out in a well equipped laboratory precluding effective on-site analysis of the samples. Considering that the hydrocarbon content of source rock and reservoir rock formations is extremely critical in determining whether to continue drilling, or to institute production procedures from the well, rapid, on-site analysis of the source rock or reservoir rock is clearly desirable.

There are other instances in which the chemical makeup of a substance is difficult to ascertain with conventional analytical techniques. For example, in the case of polymeric materials, precise chemical structure is often times impossible to ascertain. Naturally occurring chemical substances such as materials derived from plant sources also present extremely complex mixtures of chemical compounds which are difficult to analyze using conventional techniques.

In all of the instances mentioned above, analysis would be greatly facilitated if the complex chemical substances could be "taken apart," either by evolving the more volatile components from the substances and/or by breaking down the non-volatile components into compounds which are more easily identified. To this end, pyrolytic analysis has proved to be a valuable tool in the analysis of complex chemical substances.

As is well known, in a typical pyrolysis technique, the substance to be analyzed is subjected to increasing temperature so as to accomplish a selective release of the volatile components from the substance generally followed by applying a temperature at which the non-volatile components are degraded or pyrolyzed into breakdown products which are more susceptible to analysis.

Unfortunately, the pyrolysis technique suffers from several disadvantages. For one, because the volatile components or breakdown components from the substance being analyzed are at elevated temperature, they are susceptible to reaction to form other products which will give misleading results as to the composition of the original substance. Since many apparatuses used for pyrolysis employ reactive materials such as stainless steel and other metals, the volatile products and/or breakdown products can react or be adsorbed on these "chemically active" surfaces, which are at the elevated temperatures, and either be converted into other products, react with other volatile or breakdown components to form new products or be held by the adsorbent surfaces and not reach the detector.

SUMMARY OF THE INVENTION

It is therefore an object of the present invention to provide an improved apparatus for conducting pyrolytic analysis of chemical substances.

Another object of the present invention is to provide a pyrolysis apparatus useful in the analysis of chemical substances which minimizes unwanted side reactions between components or breakdown products released from the sample being analysed.

The above and other objects of the present invention will become apparent from the drawings, the description given herein and the claims.

In accordance with the above objects, there is provided a pyrolysis apparatus comprising a first, fused quartz tubular member which forms a pyrolysis chamber and has a gas outlet. There are means for introducing a sample material to be analyzed into the pyrolysis chamber and means for heating the sample material to effect pyrolysis thereof and produce gaseous components. There is also provided a means for passing a carrier gas to the pyrolysis chamber and out the gas outlet to a nozzle member which has a nozzle bore in open communication with the gas outlet. The apparatus further includes a second, fused quartz tubular member which defines a mixing chamber, the nozzle bore being in open communication with the mixing chamber whereby the carrier gas and the gaseous components pass into the mixing chamber, the second tubular member having an outlet bore in open communication with the mixing chamber. There are also, in a preferred embodiment, means, separate from the nozzle bore, for introducing a second gas into the mixing chamber, whereby the first gas, the gaseous components from the sample and the second gas pass out of the mixing chamber through the outlet bore of the second tubular member.

BRIEF DESCRIPTION OF THE DRAWINGS

FIG. 2 is a vertical section through the flame ionization chamber portion of the pyrolysis chamber according to the present invention and shown on a somewhat larger scale;

FIG. 3 is an enlarged detail of the exhaust tip where it opens into the mixing chamber;

DESCRIPTION OF THE PREFERRED EMBODIMENT

Figure 1:
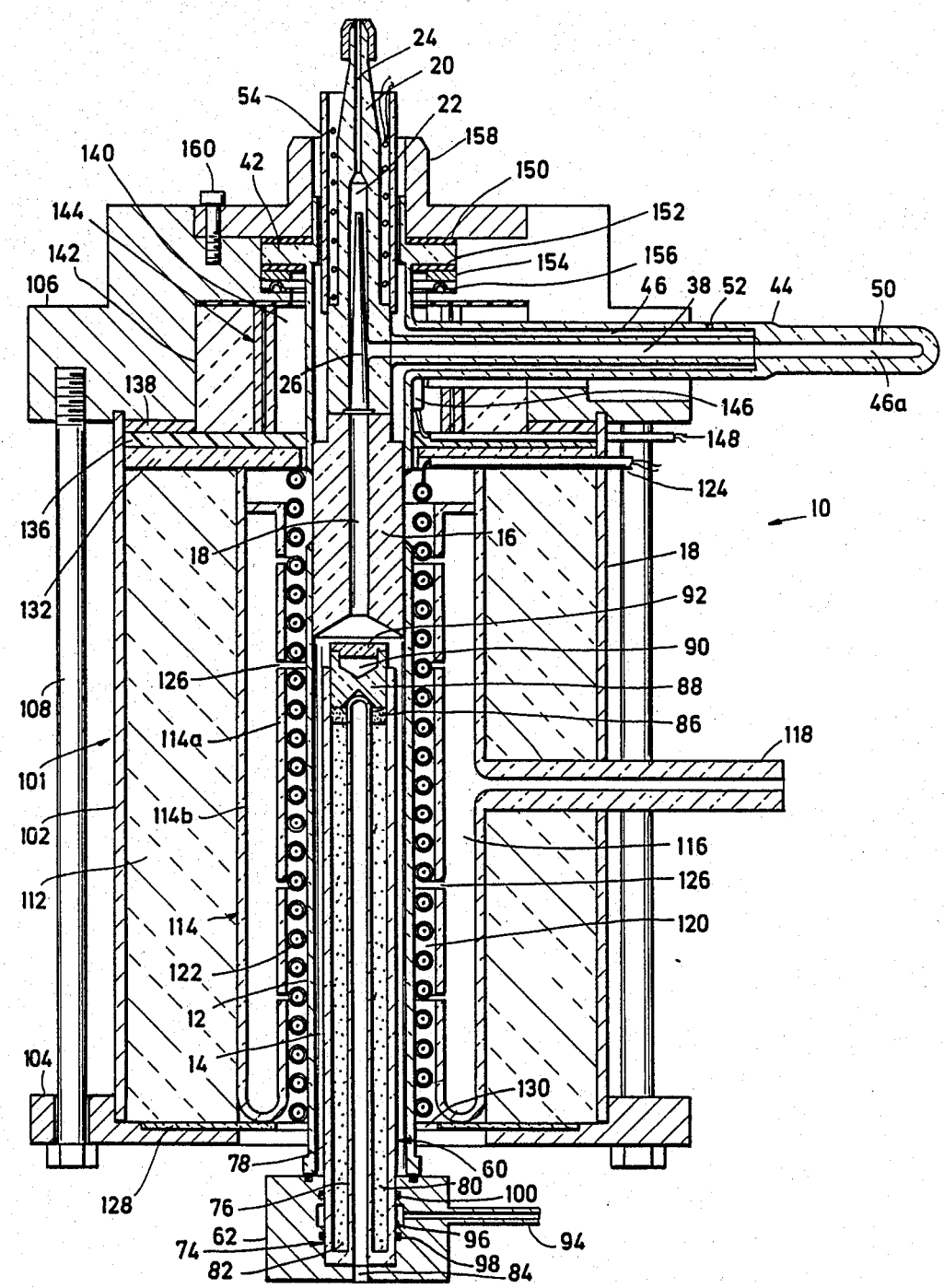
FIG. 1 is a vertical section through a pyrolysis apparatus according to the present invention.

Referring first to FIGS. 1, 2 and 3, the pyrolysis apparatus, shown generally as 10, includes a fused quartz tubular member 12 defining a pyrolysis chamber 14. Tubular member 12 is sealingly affixed, by fusing at 13, to a fused quartz spacer 16 having a bore 18 therethrough, bore 18 being in open communication with pyrolysis chamber 14. Sealingly affixed, by fusing, to a stub 15 on spacer 16 is a second fused quartz tubular member 20, tubular member 20 defining a mixing chamber 22 and being provided with an outlet bore 24, outlet bore 24 being in open communication with mixing chamber 22. Disposed in mixing chamber 22 is a fused quartz nozzle member 26, nozzle member 26 being generally conical in configuration as shown. Nozzle member 26 is provided with a conical nozzle bore 28, nozzle bore 28 being in open communication with bore 18 in spacer 16. It can thus be seen that pyrolysis chamber 14, bore 18, nozzle bore 28, mixing chamber 22 and outlet bore 24 are generally coaxial and in open communication with one another. It will also be observed, see FIG. 2, that nozzle bore 28 has an opening into mixing chamber 22 which has a smaller diameter than the diameter of bore 24 opening into mixing chamber 22, thereby preventing gases from flowing out of mixing chamber 22 into nozzle bore 28.

Second tubular member 20 terminates in a tip portion 30 provided with an electrode cap 32. Tubular member 20 also has a radial opening 34. A fused quartz tube 36 is fusibly secured to tubular member 20, tube 36 having a bore 38 which is in register with radial opening 34 in tubular member 20.

Spacer 16 is fusibly secured at 13 to a collar 40, collar 40 having a radially extending flange portion 42 and a radially outwardly extending arm 44 and defining a cavity 40a. Arm 44 defines an elongate cylindrical chamber 46 in which is received tube 36. Arm 44 also has a reduced diameter portion 44a having a bore 46a with a diameter smaller than chamber 46. Tube 36 has its end distal the end where it is adjoined to tubular member 20 fusibly affixed to an internal annular shoulder 48 in arm 44 whereby bore 38 and bore 46a are concentrically disposed in open communication with one another, the adjoining of tube 36 to abutment 48 forming chamber 46 which is isolated from bore 46a. Reduced diameter portion 44a is provided with a port 50 which communicates with bore 46a while a second port 52 communicates with chamber 46.

Concentrically secured to tubular member 20 is a cylindrical, fused quartz heater shield 54, heater shield 54 and tubular member 20 defining an annulus 56 therebetween. Disposed in annulus 56 is an electrical heating coil 58, coil 58 being wrapped around tubular member 20.

Removably receivable in pyrolysis chamber 14 of tubular member 12 is a sample tube assembly shown generally as 60. Sample tube assembly 60 comprises a metal base portion 62 which sealingly engages tubular member 12 and which supports a double walled fused quartz cylindrical member 74 having an inner tube 76 and a concentrically disposed outer tube 78, there being an annulus 80 formed therebetween. Disposed in annulus 80 is a particulate fused quartz material 82. Innermost tube 76 opens through a bore 84 in metal base 62, opening 84 serving to receive a temperature probe (not shown). A fused quartz frit 86 having a central opening for receiving innermost tube 76 serves to contain the particulate fused quartz material 82 in the annulus between tubes 76 and 78. Resting on frit 86 is a porous fused quartz sample boat 88 having a sample chamber 90 with a removable, porous fused quartz cover 92.

Metal base 62 is provided with a gas inlet 94 which communicates with an annular groove 96 surrounding outer tube 78, annular groove 96 being sealed within metal base 62 by O-rings 98 and 100. Radial ports (not shown) communicate with annular groove 96 into the annulus 80 formed between inner tube 76 and outer tube 78 whereby gas entering from gas inlet 94 can pass upwardly through the particulate fused quartz material 82 in the annulus formed between inner tube 76 and outer tube 78.

The pryolysis apparatus 10 further includes a cylindrical housing 101 having a cylindrical wall 102, a housing base 104 and a housing cap 106. Cap 106 and base 104 are secured to one another by means of bolts 108 which clamps housing wall 102 between cap 106 and base 104. Radially inward from housing 101 is an annular insulator 112 which is disposed between housing 101 and a radially inward cylindrical fused quartz cooling flask assembly 114. Cooling assembly 114 has an inner cylindrical wall 114a and an outer cylindrical wall 114b and defines an annulus 116 therebetween and in generally surrounding relationship to tubular member 12. Cooling assembly 114, which is made of fused quartz, also includes a fluid inlet 118 which extends through housing 102 and insulation 112. An annulus 120 is formed between cylindrical wall 114a of cooling assembly 114 and tubular member 12. Cooling assembly 114 is also provided with a series of radial ports 126 which provide open communication between annulus 126 and annulus 120. Disposed in annulus 120 is an electrical resistance coil 122, coil 122 being wrapped around tubular member 12. Power to coil 22 is supplied through leads 124.

Figure 4:
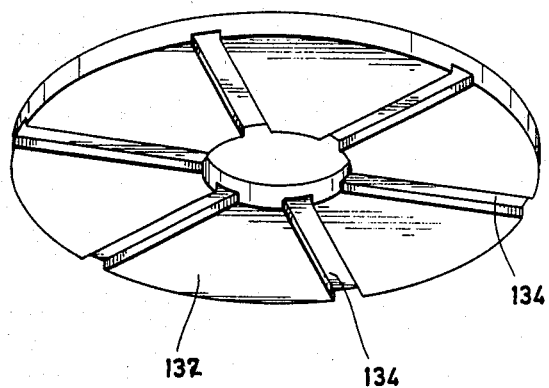
FIG. 4 is a perspective view of the spacer member showing the venting slots.
Figure 5:
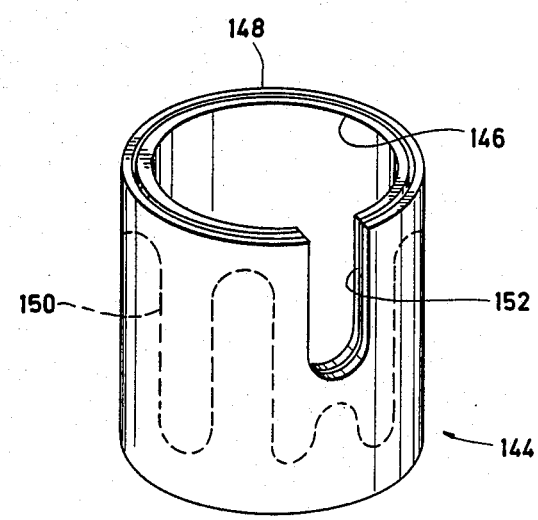
FIG. 5 is a perspective view of the flame ionization heater assembly.

An upper annular vent spacer member 132 is positioned adjacent insulation 112 and includes a plurality of radially extending grooves 134 (see FIG. 4) allowing venting of gas from the cooling assembly 114. Likewise, an insulation washer 128 disposed between base 104 and insulation 112 forms a lower annular vent 130. An insulation washer 136 and a ceramic spacer 138 are clamped between cap 106 and vent spacer 132. Cap 20 includes a recess 140 in which is received an annular insulation member 142. Also disposed in recess 140 is a heater assembly shown generally as 144 and a temperature probe 146 provided with leads 148. With reference to FIG. 5, it can be seen that heater assembly 144 comprises concentrically disposed, fused quartz cylindrical members 146 and 148 with an electrical resistance wire 150 sandwiched therebetween, heater assembly 144 being provided with a slot 152.

Flange 42 of collar 40 is sandwiched between insulation washers 150 and 152. A support washer 154 is urged against insulation washer 152 by spring washer 156. A gland member 158 secured to cap 106 by bolts 160 serves to hold the entire inner assembly stationary within housing 110.

In operation, a sample of material to be analyzed is placed in the porous sample boat 88 after which the sample tube assembly 60 is inserted into pyrolysis chamber 14 formed in tubular member 12. A carrier gas such as helium or some other inert gas is introduced into gas inlet 94 flowing upward through the quartz sand 82, through the porous frit 86 through the porous fused quartz boat 88 and into contact with the sample contained in sample chamber 90. Heating of the pyrolysis chamber 14 and hence the sample in sample boat 88 is accomplished by means of the resistance coils 122. Because cooling assembly 114 and tubular member 12 are constructed of fused quartz and transparent to infrared, the sample in sample boat 88 is rapidly heated by radiant heat emanating from the coils 122.

As the sample in boat 88 evolves volatile materials and/or is heated to a sufficiently high enough temperature to break the sample material down, the gaseous components are swept by the carrier gas from pyrolysis chamber 14 through bore 18 and into bore 28 of nozzle member 26. The mixture of carrier gas plus any components evolved from the sample exits nozzle member 26 into mixing chamber 22 where it is combined with hydrogen entering mixing chamber 22 via port 50, bore 46a and bore 38, the hydrogen entering chamber 22 in the annulus formed between nozzle member 26 and tubular member 20. The mixture of carrier gas, hydrogen and any components from the pyrolyzed sample are then forced into bore 24 of tubular member 20 exiting at tip 30. It will be understood that cap 32 is an electrical conductor forming part of a flame ionization detector and that tip 30 in cap 32 are received in a suitable, well known flame ionization detector housing. Air enters the flame ionization housing (not shown) via port 52 and bore 46, the air passing in the annulus between sleeve 54 and collar 40. The air entering the flame ionization chamber, together with the hydrogen, the carrier gas and the components released from the sample being analyzed are burned in a hydrogen, air flame which is ignited at the tip 30, the individual components from the sample being burned in the flame, thereby permitting their detection as is well known to those skilled in the art familiar with flame ionization detectors. It will be apparent that other types of detectors, such as thermal conductivity detectors, flame photometric detectors, electron capture detectors, or mass spectrometers, etc. can also be used.

It is to be observed that the carrier gas, the components evolved from the sample being analyzed and the hydrogen are all kept at a desired elevated temperature by means of heating coils 122 and 58 as well as heater assembly 144. Moreover, it is to be noted that at all times until the components from the sample exit the apparatus via tip 30, the gaseous components are only in contact with fused quartz surfaces. Accordingly, at no time do the components of the sample come into contact with reactive surfaces such as metal or other material which could change the composition or character of the components to be analyzed.

Since at all times the carrier gas and the sample components pass through bores or chambers formed by fused quartz material, they can be quickly and easily heated to a desired controlled temperature using radiant heat from the various heating coils and heater assembly 144 described above.

When it is desired to lower the temperature in the pyrolysis chamber 14, it can easily be accomplished by introducing a coolant such as liquid carbon dioxide through inlet 118 and into the annulus 116 of cooling assembly 114. The coolant can then flow through the radial ports 126 to cool the walls of tubular member 12 and hence pyrolysis chamber 14, the coolant venting via vent 130 and vent spacer member 132.

The pyrolysis apparatus of the present invention makes possible the analysis of complex chemical substances which can be converted into volatile or breakdown materials which, in and of themselves, are reactive and which, in the absence of being subjected to a constantly inert and non-adsorbent environment such as provided by fused quartz, would recombine or react to form new compounds or be adsorbed and not pass to the detectors thereby providing misleading results as to the chemical make up of the sample being analyzed.

Throughout the specification, the terms "quartz" and "fused quartz" have been used. The term "fused quartz" is intended to include material formed by direct melting of quartz crystals. "Quartz" is intended to include all forms of vitreous silica and all transparent vitreous silica as commonly understood by those skilled in the art.

It is also to be noted that while the present invention has been described as an assembly of discrete parts, this is for convenience of description only as many parts are fused together after assembly to form an integral unit.

The foregoing disclosure and description of the invention is illustrative and explanatory thereof, and various changes in the size, shape and materials as well as in the details of the illustrated construction may be made within the scope of the appended claims without departing from the spirit of the invention.

What is claimed is:

1. A pyrolysis apparatus comprising:
   a first, fused quartz tubular member defining a pyrolysis chamber having a gas outlet;
   means for introducing sample material into said pyrolysis chamber;
   means for effecting radiant heating of sample material in said pyrolysis chamber to effect pyrolysis thereof and produce gaseous components;
   means for passing a first gas stream through said pyrolysis chamber and out said gas outlet to produce a second gas stream containing gaseous components;
   a fused quartz nozzle member, said nozzle member defining a nozzle bore having an inlet and an outlet, the inlet of said nozzle bore being in open communication with said gas outlet of said pyrolysis chamber whereby the second gas stream passes through said nozzle bore;
   a second, fused quartz tubular member defining a mixing chamber having an outlet orifice, the outlet of said nozzle bore being in open communication with said mixing chamber whereby the second gas stream passes into said mixing chamber; and
   means to introduce a third gas stream into said mixing chamber;
   said outlet of said nozzle member being smaller than said outlet orifice whereby a mixture of the second gas stream and the third gas stream passes out of said mixing chamber through said outlet orifice.

2. The apparatus of claim 1 including means for cooling said pyrolysis chamber.

3. The apparatus of claim 1 wherein said means for heating comprises an electrical resistance oil surrounding said first tubular member.

4. The apparatus of claim 1 wherein said means for introducing sample material comprises:
   a fused quartz, cylindrical member having a first end and a second end and receivable in said pyrolysis chamber;
   a gas porous fused quartz sample boat removably received in said first end of said cylindrical member for containing the sample material;
   means for introducing the first gas into said cylindrical member near said second end of said cylindrical member distal said sample boat; and
   particulate fused quartz received in said cylindrical member between said sample boat and said second end, whereby the first gas flows over said particulate fused quartz and through said sample boat.

* * * * *